United States Patent [19]

Muller et al.

[11] 4,421,856

[45] * Dec. 20, 1983

[54] FERMENTABLE SUGAR FROM THE HYDROLYSIS OF CARBOHYDRATE POLYMER

[75] Inventors: Werner C. Muller, Dobbs Ferry, N.Y.; Franklyn D. Miller, Cincinnati, Ohio

[73] Assignee: National Distillers and Chemical Corporation, New York, N.Y.

[*] Notice: The portion of the term of this patent subsequent to Sep. 1, 1998 has been disclaimed.

[21] Appl. No.: 320,277

[22] Filed: Nov. 12, 1981

[51] Int. Cl.³ .............................................. C13K 1/06
[52] U.S. Cl. .................................. 435/161; 435/165; 127/37; 127/38; 127/40; 203/19; 203/DIG. 13

[58] Field of Search ...................... 435/161, 163, 165; 127/37, 38, 39, 40, 36, 56; 203/19, DIG. 13

[56] References Cited

U.S. PATENT DOCUMENTS 4,287,304  9/1981  Muller et al. .................. 435/161
4,330,625  5/1982  Miller et al. .................. 435/161

*Primary Examiner*—William F. Smith
*Attorney, Agent, or Firm*—Kenneth D. Tremain

[57] ABSTRACT

The yield of fermentable sugar, largely glucose (dextrose), resulting from the acid catalyzed hydrolysis of a carbohydrate polymer such as starch or cellulose can be significantly increased by the addition to the hydrolysate under acid hydrolysis conditions of water soluble non-fermentable carbohydrate such as stillage recovered from a downstream ethanol distillation facility.

9 Claims, 1 Drawing Figure

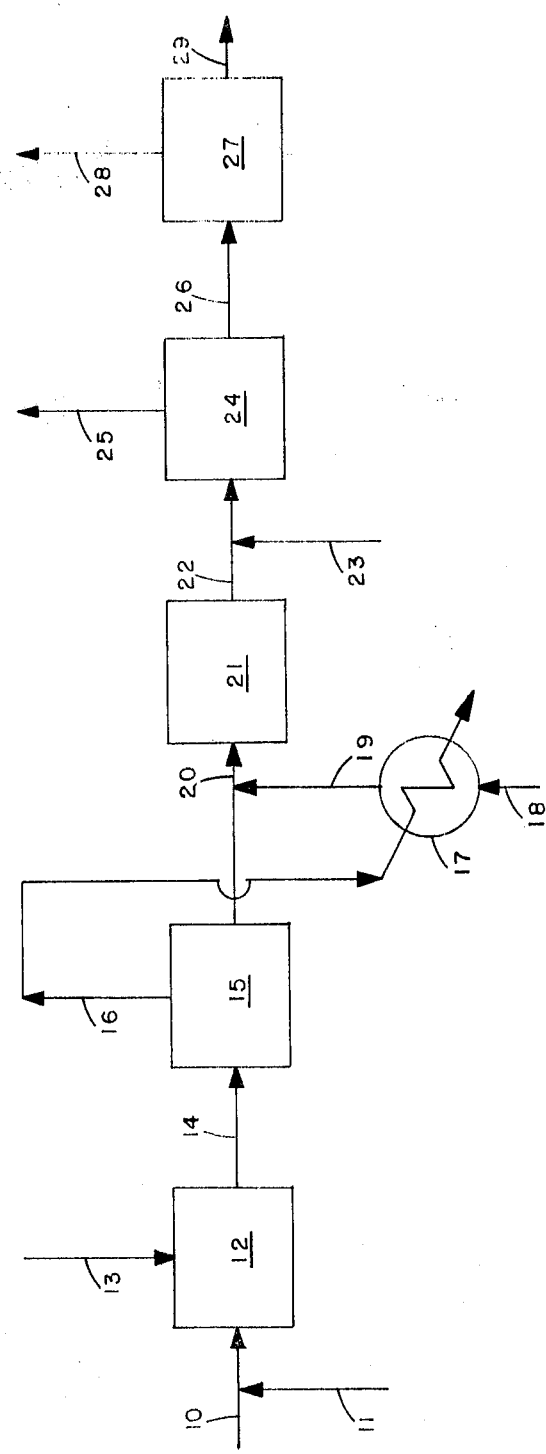

FERMENTABLE SUGAR FROM THE HYDROLYSIS OF CARBOHYDRATE POLYMER

REFERENCE TO RELATED APPLICATIONS

This application discloses subject matter which is disclosed and claimed in commonly assigned U.S. Pat. No. 4,247,638, filed May 29, 1979, U.S. Pat. No. 4,255,518, U.S. patent application Ser. No. 91,640 filed Nov. 5, 1979 now abandoned in favor of copending U.S. patent application Ser. No. 237,038, filed Feb. 23, 1981 and U.S. Pat. application Ser. No. 320,278 filed of even date herewith.

BACKGROUND OF THE INVENTION

This invention relates to the acid hydrolysis of aqueous slurries of carbohydrates such as starches derived from cereal grains, amylaceous roots and tubers, and cellulose in the form of saw dust, wood chips, bark, paper, rags, etc.

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficent fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity consumed and versatility in product synthesis.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of sugar to a dilute solution of ethanol ("beer") and the recovery of anhydrous ethanol by distillation, have been modified in numerous ways to achieve improvements in product yield, production rates and so forth (see, for example, U.S. Pat. No. 3,236,740 and the booklet "Industrial Alcohol by Continous Fermentation and Vacuum Distillation With Low Energy Consumption", of Chemapec, Inc., Woodbury, New York). For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of the ethanol as an economically viable replacement for petroleum based raw materials. To date, however, relatively little concern has been given to the energy and raw material requirements for manufacturing ethanol from biomass and consequently, little effort has been made to minimize the thermal expenditure and waste incurred in carrying out any of the aforesaid discrete operations involved in the manufacture of ethanol from vegetative sources.

Processes for the acid hydrolysis of carbohydrate polymers i.e., starch and cellulose, to provide fermentable sugars are known (viz., U.S. Pat. Nos. 2,203,325; 2,210,659; 2,359,763; 2,393,095; 2,395,907; 2,529,131; 2,565,404; 2,946,706; 2,954,304; 2,989,425; 3,169,083; 3,200,012; 3,236,687; 3,313,654; 3,446,664; 3,484,287; 3,607,395; 4,137,094; and, 4,155,884).

In addition to the desired reaction whereby the carbohydrate polymer molecules are split into fermentable sugars, other reactions taking place during hydrolysis tend to reduce the maximum theoretical conversion of available carbohydrate to such sugars and produce non-fermentable hydrolysate products. Three of the principle types of undesirable reactions known to take place in acid catalyzed carbohydrate polymer hydrolysis are: degradation (starch molecule is irreversibly destroyed to provide 5-hydroxymethylfurfural which hydrolyzes to levulinic acid and formic acid, and separately polymerizes to humins); reversion (glucose repolymerizes and/or isomerizes to unfermentable substances); and retrogradation (hydrolysis splits out the branched chain components of the starch molecule leaving a straight chain, lower molecular weight water insoluble polymeric molecule which crystallizes at about 70°–80° C. and becomes resistant to further hydrolysis). In a typical acid hydrolysis process, when equilibrium has been achieved, from about 15 to about 20 weight percent of the depolymerized starch will be present in the form of one or more of the foregoing non-fermentable hydrolysates, the balance of the depolymerized starch being present as glucose and/or other fermentable sugar(s). To the extent nonfermentable products are produced side-by-side with fermentable sugar(s), they represent a loss in yield of the hydrolysis reaction and compromise the usefulness of acid hydrolysis as a process for obtaining fermentable sugar on a large-scale, economical basis.

According to U.S. Pat. No. 2,529,131 referred to supra, the non-fermentable hydrolysate products resulting from one or more of the aforesaid undesirable reactions eventually is recovered in the stillage, or "vinasse", obtained as a result of the distillation of the dilute ethanol, or "beer", resulting from the fermentation of the fermentable sugar portion of the hydrolysate. To maximize overall ethanol production, based on the original quantity of carbohydrate polymer employed, it is proposed in U.S. Pat. No. 2,529,131 to subject the stillage to further acid hydrolysis to convert the unfermentable products therein to fermentable sugars.

SUMMARY OF THE INVENTION

It has now been discovered that the yield of fermentable sugar, largely glucose (dextrose), obtained as a result of the acid catalyzed hydrolysis of carbohydrate polymer can be significantly increased by the addition to the hydrolysate, under acid hydrolysis conditions, of an aqueous water soluble non-fermentable carbohydrate, e.g., any of the degradation, reversion and/or retrogradation products referred to above, whereby a sterile, substantially fully hydrolyzed slurry of high fermentable sugar content is obtained. The presence of aqueous water soluble non-fermentable carbohydrate (which is recovered as stillage and/or as repulped supernatant from the conversion of a previous quantity of starch to concentrated ethanol) at the commencement of hydrolysis provides several very significant advantages each of which results in a greater overall production of fermentable sugar when a steady-state process has been achieved. For one, the presence of non-fermentable carbohydrate during hydrolysis reequilibrates the hydrolysate with the result that higher conversion levels of partial hydrolysate to fermentable sugar are obtained. For another, the addition of more water (the solvent medium for the non-fermentable carbohydrate) to the hydrolysate medium lowers its solids content whereby the equilibrium of the hydrolysis reaction is shifted still further to the production of fermentable sugar.

In accordance with the process of the present invention, an aqueous slurry of carbohydrate polymer, e.g., an aqueous slurry of manioc root starch or other amylaceous root starch obtained from the starch recovery process of U.S. Pat. No. 4,247,638 or an aqueous slurry of corn starch, milo starch or other cereal grain starch obtained from the wet milling process of U.S. Pat. No. 4,255,518, both of which are incorporated by reference herein, is subjected to an acid catalyzed hydrolysis, advantageously in accordance with the process described in Ser. No. 91,640 filed Nov. 5, 1979, now abandoned in favor of copending U.S. patent application Ser. No. 237,038, filed Feb. 23, 1981 which is incorporated by reference herein (employing, inter alia, elevated pressure and temperature), in the presence of added water soluble non-fermentable carbohydrate, preferably in the form of stillage obtained from a downstream ethanol concentration facility, to provide a sterile starch hydrolysate. Hydrolysis can, if desired, be carried out in a series of stages with non-fermentable carbohydrate being added at one or all hydrolysis stages. As a result of the aforesaid hydrolysis, the bulk of the carbohydrate polymer is depolymerized to fermentable sugar together with the formation of some unfermentable carbohydrate products as aforedescribed. Following hydrolysis but before the fermentable sugar present in the hydrolysate slurry is introduced into a fermenter, the acid hydrolysis catalyst must be removed or otherwise neutralized to a level of pH tolerable to fermentation, e.g., pH 4.0, with any suitable base such as ammonia, alkali metal hydroxide, alkaline earth metal hydroxide, or the like. It is, of course, advantageous to neutralize the hydrolysate slurry prior to the removal of the water insoluble proteins, fiber and oil therein.

The term "fermentable sugar" as used herein is to be understood as referring to a single fermentable sugar such as glucose (dextrose), fructose, or sucrose but more commonly will be applicable to these and similar fermentable sugars and fermentable sugar oligomers in admixture.

BRIEF DESCRIPTION OF THE DRAWING

The accompanying drawing is a diagrammatic flow sheet illustrative of the carbohydrate polymer hydrolysis process of the present invention as applied to wet milled corn or milo starch and employing two hydrolysis stages. The process contemplates the use of known and conventional equipment which is readily available from several suppliers.

DESCRIPTION OF THE PREFERRED EMBODIMENTS

Referring to the drawing, an aqueous slurry of corn or milo starch containing, on a dry basis, from about 20% to about 50% starch, and preferably from about 30% to about 40% starch, by weight of the entire slurry is conveyed through line 10 where it is admixed with a catalytically effective amount of a strong acid to provide a pH of from about 1.0 to about 2.5. The acidified starch slurry is then introduced into preliminary hydrolysis unit 12 under pressure and hydrolysis is carried out therein in the presence of steam injected through line 13. The pressure imparted to the slurry can vary over fairly wide limits but in any event must be a pressure which is in excess of the saturation pressure of water at the temperature of the hydrolysate steam passing through line 14, preferably by at least about 50 psig. Pressures on the order of from about 100 to about 1,000 psig and advantageously, from about 600 to about 900 psig, generally provide good results. The amount of steam delivered to hydrolysis unit 12 should be sufficient to increase the temperature of the slurry which, in the case of starch, can be in the range of from about 140° C. to about 220° C., and preferably, from about 160° C. to about 200° C., and in the case of cellulose, can be in the range of from about 180° C. to about 290° C., and preferably, from about 220° C. to about 270° C. Residence time of the starch slurry in preliminary hydrolysis unit 12 to effect substantial hydrolysis and sterilization of the starch is not a critical consideration. In general, residence times of just a few seconds, e.g., from about 10 seconds up to about 15 minutes or more, provide good results. The partially hydrolyzed starch slurry is then conveyed through line 14 to a first pressure reduction vessel 15 in which a partial pressure reduction takes place to partially cool the slurry for the further, and final, hydrolysis step. In the embodiment of the process shown in the drawing, steam generated by the foregoing partial pressure reduction operation recovered through line 16 is advantageously passed through heat exchanger 17 to preheat the stillage and/or the corn-/milo steepwater stream passing through line 18. In addition to or in lieu of the foregoing, it is within the scope of this invention to introduce the stillage and/or corn/milo steepwater through line 19 to be combined with the carbohydrate polymer slurry passing through line 10 into preliminary hydrolysis unit 12. Emerging from heat exchanger 17 through line 19, the pre-heated stillage/steepwater is combined with the sterile hydrolysate in line 20 and the mixture is introduced into final hydrolysis unit 21 in which the distribution of the sugars is altered in favor of glucose due to the presence of water soluble non-fermentable carbohydrates present in the added stillage/steepwater. Thus, instead of a final dextrose equivalent (D.E.) of about 75–80 which would result from conventional acid hydrolysis processes, the hydrolysis herein typically provides D.E. levels of from about 85–90 and even higher based on the carbohydrate feed and stillage/steepwater stream. The second hydrolysis step can be carried out under the same conditions as the preliminary hydrolysis step but preferably is carried out at reduced pressure and temperature, e.g., from about 50–100 psig and 120°–150° C. Duration of the second hydrolysis can vary widely, e.g., from about 3 minutes to about 2 hours or more and preferably from about 5 to about 15 minutes. The aqueous hydrolysate passing through line 22, now at its maximum fermentable sugar content for the conditions chosen, is combined with an amount of base, e.g., ammonia or ammonium hydroxide, supplied through line 23 sufficient to neutralize the hydrolysate to a pH level suitable for fermentation and the neutralized hydrolysate is reduced to atmospheric pressure in a second pressure reduction vessel 24 which results in still further cooling thereof. Of course, it is within the scope of this invention to subject the hydrolysate slurry to pressure reduction prior to effecting neutralization with base or ion exchange. Regenerated steam recovered from 24 through line 25 is advantageously employed elsewhere in the process or in some other plant facility where it can be effectively utilized. When the salt resulting from neutralization of the acid is recycled (as will be the case when stillage is added to the initial starch slurry/partial starch hydrolysate), a buffering action results so that it becomes necessary to add still higher levels of acid to achieve a pH which is appropriate for hydrolysis. Such higher levels of acid result in the production of still more salt which results in an even greater buffering action. Accordingly, in may be advantageous to contact the stillage with a strong acid cation exchange resin, e.g., Dow's Dowex MWA-1 and XFS-4066 which are copolymers of styrene and divinylbenzene with controlled crosslinkage in order to remove cations, e.g., $NH_4^+$, and regenerate acid. The depressurized, neutralized aqueous hydrolysate (sugar liquor) is advantageously passed through line 26 into vacuum flash cooler 27 (or other cooling device), water vapor being discharged therefrom to the atmosphere through line 28. The sterile aqueous sugar, now at a temperature and pH which is advantageously conducive to an optimized fermentation process, is introduced through line 29 into one or more fermentation vessels for conversion to ethanol. Alternatively, the sugar liquor can be introduced to storage.

The following represents a material balance (lb/hr) for various stages of the process herein as applied to food grade corn starch.

What is claimed is:

1. In the acid hydrolysis of carbohydrate polymer in which an aqueous slurry of carbohydrate polymer selected from the group consisting of starch and cellulose is hydrolyzed at elevated pressure and temperature in the presence of an acid catalyst to provide a hydrolysate comprising a sterile aqueous solution of fermentable sugar, the improvement which comprises carrying out hydrolysis in the presence of added aqueous water soluble non-fermentable carbohydrate.

2. The process of claim 1 wherein a preliminary hydrolysis step is followed by a further hydrolysis step and following said preliminary hydrolysis the temperature and pressure of the partial hydrolysate is at least partially reduced.

3. The process of claim 1 wherein the carbohydrate polymer is starch derived from wet milled cereal grain or starch derived from amylaceous root or tuber.

4. The process of claim 1 wherein the carbohydrate polymer is cellulose.

5. The process of claim 1 wherein the carbohydrate polymer is starch derived from wet milled corn or milo.

6. The process of claim 1 wherein the hydrolysate is fermented to provide dilute aqueous ethanol, the dilute aqueous ethanol is concentrated by distillation and the stillage resulting from said distillation is used as the source of added water soluble non-fermentable carbohydrate in the hydrolysis of a further quantity of hydrolysate.

7. The process of claim 1 wherein the carbohydrate polymer feed is slurried with stillage.

8. The process of claim 6 wherein the acid hydrolysis catalyst is neutralized with base prior to subjecting the hydrolysate to fermentation.

9. The process of claim 8 wherein salt resulting from neutralization of hydrolysis catalyst is reconverted to acid by contact with a strong acid ion exchange resin.

* * * * *

| | | | | | | | |
|---|---|---|---|---|---|---|---|
| ACID HYDROLYSIS OF CORN STARCH TO PROVIDE STERILE AQUEOUS FERMENTABLE SUGAR | | | | | | | |
| STREAM/DESCRIPTION | | | | | | | |
| COMPONENT | 10 Starch Feed | 11 Acid | 13 Steam | 14 Hydrolyzed Starch | 18 Stillage | 20 Feed to Equilibration Vessel | 22 Equilibrated Hydrolysate | 29 Sugar Solution |
| Water/Steam | 62,803 | 4 | 39,171 | 97,296 | 122,067 | 203,571 | 203,571 | 161,056 |
| Ethanol | — | — | — | — | 32 | 32 | 32 | 32 |
| Glycerol | — | — | — | — | 6,583 | 6,583 | 6,583 | 6,583 |
| Starch | 42,150 | — | — | — | — | — | — | — |
| Fermentable Sugar* | — | — | — | 23,416 | 308 | 23,724 | 44,936 | 44,936 |
| Sugar Oligomers | — | — | — | 23,416 | 6,999 | 30,415 | 9,203 | 9,203 |
| Protein & Fiber | 190 | — | — | 190 | 13 | 203 | 203 | 203 |
| Sulfuric Acid | — | 211 | — | 211 | 664 | 875 | 875 | — |
| Ammonium Sulfate | — | — | — | — | — | — | — | 1179 |
| Yeast | — | — | — | — | 264 | 264 | 264 | 264 |
| TOTAL | 105,143 | 215 | 39,171 | 144,529 | 136,930 | 265,667 | 265,667 | 223,456 |

*Calculated as glucose.